United States Patent
Li et al.

(10) Patent No.: US 10,946,365 B2
(45) Date of Patent: Mar. 16, 2021

(54) MATERIALS AND METHODS FOR OXIDATIVE DEHYDROGENATION OF ALKYL AROMATIC COMPOUNDS INVOLVING LATTICE OXYGEN OF TRANSITION METAL OXIDES

(71) Applicant: North Carolina State University, Raleigh, NC (US)

(72) Inventors: Fanxing Li, Raleigh, NC (US); Xing Zhu, Raleigh, NC (US); Yunfei Gao, Raleigh, NC (US)

(73) Assignee: North Carolina State University Office of Research, Raleigh, NC (US)

( * ) Notice: Subject to any disclaimer, the term of this patent is extended or adjusted under 35 U.S.C. 154(b) by 0 days.

(21) Appl. No.: 16/506,351

(22) Filed: Jul. 9, 2019

(65) Prior Publication Data

US 2020/0009539 A1   Jan. 9, 2020

Related U.S. Application Data

(60) Provisional application No. 62/695,245, filed on Jul. 9, 2018.

(51) Int. Cl.
*C07C 5/48* (2006.01)
*B01J 23/889* (2006.01)
(Continued)

(52) U.S. Cl.
CPC ......... *B01J 23/8892* (2013.01); *B01J 23/002* (2013.01); *B01J 23/04* (2013.01); *B01J 23/22* (2013.01); *B01J 23/34* (2013.01); *B01J 23/745* (2013.01); *B01J 23/78* (2013.01); *B01J 23/83* (2013.01); *B01J 35/12* (2013.01);
(Continued)

(58) Field of Classification Search
CPC ......... C07C 5/42; C07C 11/167; C07C 15/44; C07C 15/46; C07C 2521/10; C07C 2523/02; C07C 2523/04; C07C 2523/22; C07C 2523/34; C07C 2523/745; C07C 2523/78; C07C 2523/889; C07C 5/48; B01J 23/002; B01J 23/04; B01J 23/22; B01J 23/34; B01J 23/745; B01J 23/78;
(Continued)

(56) References Cited

U.S. PATENT DOCUMENTS 9,884,313 B2 *  2/2018  Shen .................... C07C 2/84

* cited by examiner

*Primary Examiner* — Sharon Pregler
(74) *Attorney, Agent, or Firm* — Thomas|Horstemeyer, LLP

(57) ABSTRACT

In one aspect, the disclosure relates to a process for dehydrogenating a first dehydrogenation reactant into its unsaturated counterparts. The disclosed process comprises introducing a dehydrogenation reactant to a metal oxide catalyst having dehydrogenation activity, and dehydrogenating the dehydrogenation reactant to provide its unsaturated counterpart and hydrogen; selectively combusting the hydrogen released during dehydrogenation using a lattice oxygen from the metal oxide catalyst, resulting in a reduced metal oxide catalyst and steam; re-oxidizing the reduced metal oxide catalyst by introducing a gaseous oxidant to the reduced metal oxide catalyst; and optionally re-using the re-oxidized metal oxide catalyst for catalytic conversion and combustion. This abstract is intended as a scanning tool for purposes of searching in the particular art and is not intended to be limiting of the present disclosure.

20 Claims, 5 Drawing Sheets

(51) Int. Cl.
*B01J 23/745* (2006.01)
*B01J 23/78* (2006.01)
*B01J 35/12* (2006.01)
*B01J 23/00* (2006.01)
*B01J 23/34* (2006.01)
*B01J 23/22* (2006.01)
*B01J 23/83* (2006.01)
*B01J 37/03* (2006.01)
*B01J 37/08* (2006.01)
*B01J 37/02* (2006.01)
*B01J 23/04* (2006.01)

(52) U.S. Cl.
CPC ......... *B01J 37/0207* (2013.01); *B01J 37/036* (2013.01); *B01J 37/088* (2013.01); *C07C 5/48* (2013.01); *C07C 2521/10* (2013.01); *C07C 2523/02* (2013.01); *C07C 2523/04* (2013.01); *C07C 2523/22* (2013.01); *C07C 2523/34* (2013.01); *C07C 2523/745* (2013.01); *C07C 2523/78* (2013.01)

(58) Field of Classification Search
CPC ........ B01J 23/83; B01J 23/8892; B01J 35/12; B01J 37/0207; B01J 37/036; B01J 37/088
See application file for complete search history.

MATERIALS AND METHODS FOR OXIDATIVE DEHYDROGENATION OF ALKYL AROMATIC COMPOUNDS INVOLVING LATTICE OXYGEN OF TRANSITION METAL OXIDES

CROSS-REFERENCE TO RELATED APPLICATIONS

This Application claims the benefit of U.S. Provisional Application No. 62/695,245, filed on Jul. 9, 2018, which is incorporated herein by reference in its entirety.

STATEMENT REGARDING FEDERALLY SPONSORED RESEARCH

This invention was made with government support under grant number 1604605 awarded by the National Science Foundation. The government has certain rights in the invention.

BACKGROUND

Alkyl aromatic compounds are important industrial chemical feedstock. They are often produced from tar, petroleum cracking, and aromatization. Conversion of alkyl aromatic hydrocarbons to their unsaturated counterparts plays a very important role for the production of various important materials and chemicals such as polystyrene (PS), poly-α-methyl styrene resin (PaMS), etc. Styrene is one of the most important feedstock in the production of rubber and plastic components, which is mainly produced from dehydrogenation of ethylbenzene.

It has been reported that global styrene production exceeded 26.4 million Tonnes in 2012, and it has increased over the past five years. Direct dehydrogenation of ethylbenzene technology produces 90% of styrene at present and its dominance is likely to last well into the future. Ethylbenzene dehydrogenation has been developed in the past decades in the aspects of catalyst and reactor systems.

Nevertheless, ethylbenzene dehydrogenation suffers from high energy consumption, equilibrium limitations, and complex separation due to: 1) The endothermic and equilibrium limited dehydrogenation reaction; 2) The need for steam co-feed; and 3) Downstream product separation requirements due to the significant amount of hydrogen (and other gaseous byproducts) generated. Taking the industrial applications of ethylbenzene dehydrogenation processes as examples, commercially-available technologies such as those available from ABB Lummus/UOP, Fina/Badger, and BASF, involve co-feeding a large amount of steam as heat carrier and reaction atmosphere in the catalytic dehydrogenation process. Attempts have been made to apply an oxidative dehydrogenation approach by co-feeding gaseous oxygen to selectively combust hydrogen products from the dehydrogenation reaction. Commercially-available examples include the UOP Styro-Plus and Lummus/UOP Smart SM™ processes. These technologies still rely on a co-feed of steam when oxygen or air are used as the oxidants for selective hydrogen combustion from dehydrogenation. Co-feeding gaseous oxygen can result in safety concerns and air separation can be expensive.

Moreover, product selectivity and effectiveness of heat integration can be limited in these cases. These drawbacks also exist in the dehydrogenation of cumene to α-methylstyrene, and more generally to dehydrogenation of other alkyl aromatic compounds, due to the similarity of the processes. Thus, the typical commercially-available industrial applications have to use a second hydrogen (or other fuel) combustion reactor, high steam/feedstock ratios to offset the heat for the endothermic reaction, and complex reaction systems for heat management or products separation, leading to the loss of efficiency, high running cost, high energy consumption, as well as high carbon emissions. In addition, the equilibrium limitation leads to less than optimal product yields.

Despite recent advances, there is still a scarcity of processes that are both safe and efficient in the dehydrogenation of alkyl aromatic compounds. These needs and other needs are satisfied by the present disclosure.

The description herein of certain advantages and disadvantages of known methods and devices is not intended to limit the scope of the present invention. Indeed the present embodiments may include some or all of the features described above without suffering from the same disadvantages.

SUMMARY

In accordance with the purpose(s) of the disclosure, as embodied and broadly described herein, the disclosure, in one aspect, relates to a process for oxidative dehydrogenation, comprising: a) introducing one or more dehydrogenation reactants to a metal oxide catalyst having dehydrogenation activity, and dehydrogenating the one or more dehydrogenation reactants to provide a dehydrogenated reaction product and hydrogen; b) selectively combusting the hydrogen released during dehydrogenation using a lattice oxygen from the metal oxide catalyst, resulting in a reduced metal oxide catalyst and steam; c) re-oxidizing the reduced metal oxide catalyst by introducing a gaseous oxidant to the reduced metal oxide catalyst; and optionally d) re-using the re-oxidized metal oxide catalyst for a subsequent dehydrogenation and/or selective combustion. Optionally, the dehydrogenation reactants comprise an alkyl aromatic hydrocarbon or a substituted alkyl aromatic hydrocarbon and the dehydrogenated reaction product comprises an alkene aromatic hydrocarbon or substituted alkene aromatic hydrocarbon, respectively. Optionally, the dehydrogenation reactants comprise an alkyl naphthalene and the dehydrogenated reaction product comprises an alkene naphthalene. Optionally, the dehydrogenation reactants comprise an alkyl furan, alkyl pyrrole, alkyl thiophene, or alkyl pyridine, and the dehydrogenated product comprises alkene furan, alkene pyrrole, alkene thiophene, or alkene pyridine, respectively. Optionally, the dehydrogenation reactants comprise a 1-butene or 2-butene, and the dehydrogenation product comprises 1,3-butadiene.

In another aspect, the disclosure relates to a redox catalyst comprising a catalytic dehydrogenation component and a hydrogen selective combustion component, wherein the catalytic dehydrogenation and hydrogen selective combustion components comprise a single metal oxide particle, two or more mixed metal oxides particles, or two or more independent metal oxides particles.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figures 1A, 1B:
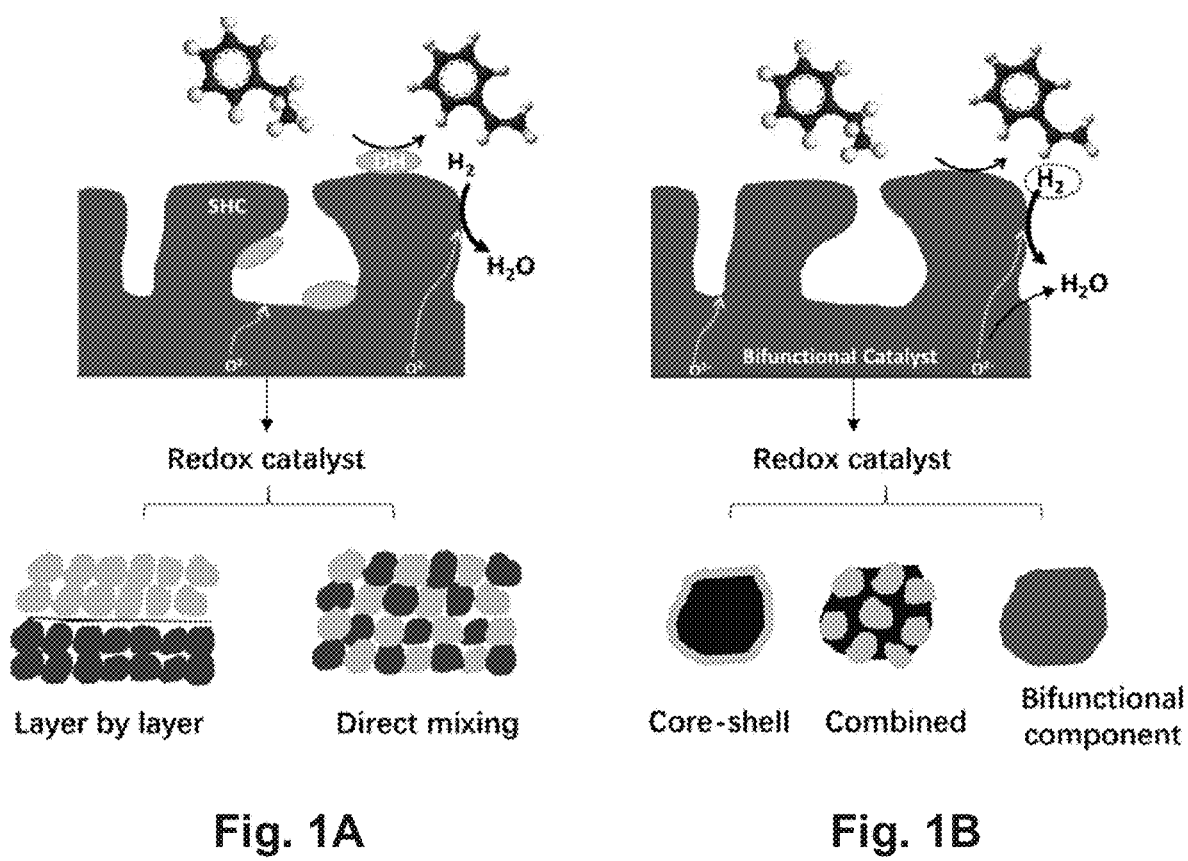
FIGS. 1A-1B show an example of redox catalyst design according to embodiments of the present disclosure and its reaction mechanism in R-ODH (Taken ODH of ethylbenzene to styrene as an example). Light and dark colors correspond to dehydrogenation (DH) component and selective hydrogen combustion (SHC) component, respectively. In the core-shell illustration case (FIG. 1B), the darker color also corresponds to materials that are bifunctional (DH+SHC).

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The disclosure herein generally relates to a processes, methods, and materials for redox oxidative dehydrogenation (R-ODH). The disclosed R-ODH processes address the drawbacks discussed above with respect to commercially-available dehydrogenation technologies. More specifically, the disclosed R-ODH processes use a specially-designed redox catalyst. According to certain disclosed aspects, the processes, methods and materials may pertain more specifically to the R-ODH of alkyl aromatic hydrocarbons. For example, according to the disclosed aspects, alkyl aromatic hydrocarbons can be catalytically converted into alkene aromatic hydrocarbons and water through dehydrogenation. According to the various disclosed aspects, the dehydrogenation may be coupled with a simultaneous or sequential selective hydrogen combustion (SHC) using a lattice oxygen donated by redox catalysts. The redox catalysts are then replenished with air or other suitable oxidizing gas such as $CO_2$ or steam (also known as an oxidant).

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

B. Redox Oxidative Dehydrogenation (R-ODH)

The various aspects disclosed herein pertain to methods and redox catalyst for redox oxidative dehydrogenation (R-ODH) of certain reactants. For example, according to various disclosed aspects, alkyl aromatic hydrocarbons can be catalytically converted into alkene aromatic hydrocarbons and water through dehydrogenation.

In an aspect, the disclosure pertains to R-ODH of ethylbenzene to styrene.

In another aspect, the disclosure pertains to R-ODH of ethylbenzene with substituted benzene ring as illustrated in (I) below:

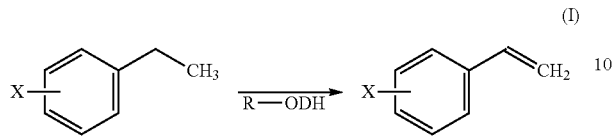

(I)

Where X is a substituting group=—CH$_3$ or other alkyl group, —CH=CH$_2$ or other alkenyl group, —C$_6$H$_5$ or other benzyl group, —NO$_2$, —NH$_2$, —NR$_2$, —OH, —COR, —CN, —CO$_2$R, —SO$_3$H, —F, —Cl—, —Br, —I; or any combination thereof. In this description, R is alkyl group (—C$_n$H$_{2n+1}$). In this aspect, the number of substituting groups (X) can be from 1 to 5.

In an aspect, the disclosure pertains to R-ODH of cumene to α-methylstyrene.

In another aspect, the disclosure pertains to R-ODH of cumene with substituted benzene ring as illustrated in (II) below:

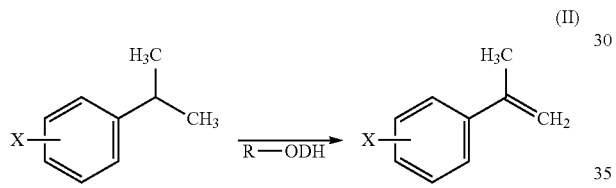

(II)

Where X is a substituting group=—CH$_3$ or other alkyl group, —CH=CH$_2$ or other alkenyl group, —C$_6$H$_5$ or other benzyl group, —NO$_2$, —NH$_2$, —NR$_2$, —OH, —COR, —CN, —CO$_2$R, —SO$_3$H, —F, —Cl—, —Br, —I; or any combination thereof. In this description, R is alkyl group (—C$_n$H$_{2n+1}$). In this aspect, the number of substituting groups (X) can be from 1 to 5.

In an aspect, the disclosure pertains to R-ODH of ethyl-naphtylene to ethenyl-naphthalene.

In another aspect, the disclosure pertains to R-ODH of ethyl-naphthalene with substituted benzene ring as illustrated in (III) below:

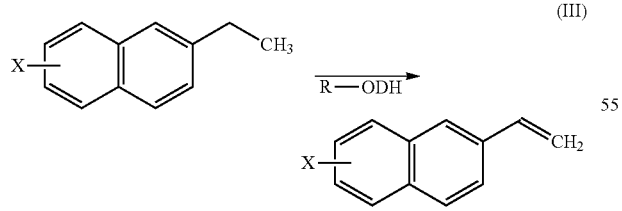

(III)

Where X is a substituting group=—CH$_3$ or other alkyl group, —CH=CH$_2$ or other alkenyl group, —C$_6$H$_5$ or other benzyl group, —NO$_2$, —NH$_2$, —NR$_2$, —OH, —COR, —CN, —CO$_2$R, —SO$_3$H, —F, —Cl—, —Br, —I; or any combination thereof. In this description, R is alkyl group (—C$_n$H$_{2n+1}$). In this aspect, the number of substituting groups (X) can be from 1 to 7.

In an aspect, the disclosure pertains to R-ODH of isopropyl-naphthalene to isopropenyl-naphthalene.

In another aspect, the disclosure pertains to R-ODH of isopropyl-naphthalene with substituted benzene ring as illustrated in (IV) below:

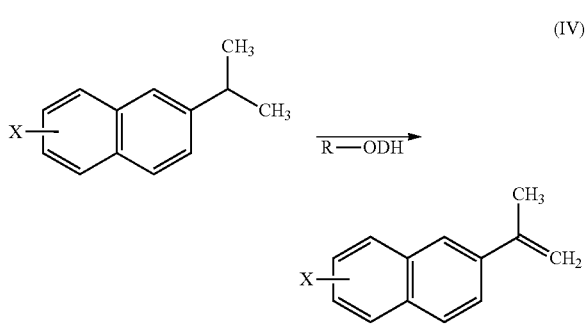

(IV)

Where X is a substituting group=—CH$_3$ or other alkyl group, —CH=CH$_2$ or other alkenyl group, —C$_6$H$_5$ or other benzyl group, —NO$_2$, —NH$_2$, —NR$_2$, —OH, —COR, —CN, —CO$_2$R, —SO$_3$H, —F, —Cl—, —Br, —I; or any combination thereof. In this description, R is alkyl group (—C$_n$H$_{2n+1}$). In this aspect, the number of substituting groups (X) be from 1 to 7.

Besides alkyl aromatic hydrocarbons, in other aspects, the various methods and catalysts described in this disclosure also may pertain to R-ODH of one or more of: ethyl furan or isopropyl furan; ethyl pyrrole or isopropyl pyrrole; ethyl thiophene or isopropyl thiophene; ethyl pyridine or isopropyl pyridine; as illustrated in (V) to (VIII), respectively, below:

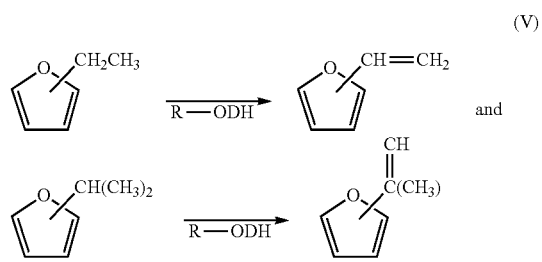

(V)

where the ethyl or the isopropyl group can be linked to any carbon atom on the furan ring;

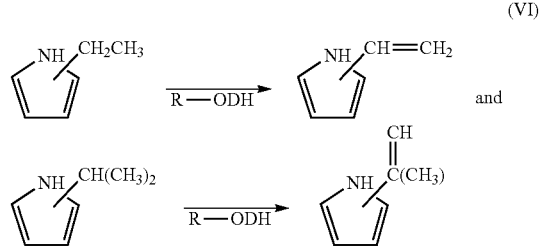

(VI)

where the ethyl or the isopropyl group can be linked to any carbon atom on the pyrrole ring;

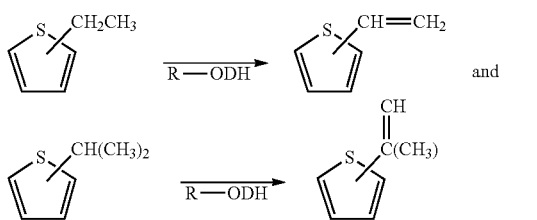

(VII)

where the ethyl or the isopropyl group can be linked to any carbon atom on the thiophene ring;

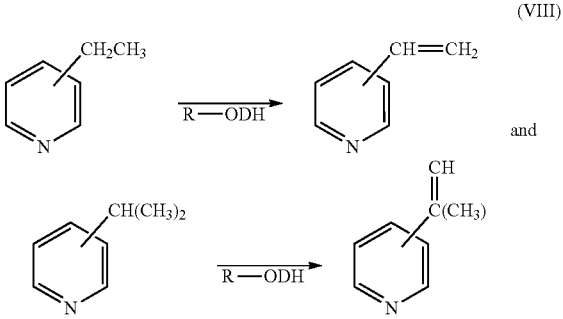

(VIII)

where the ethyl or the isopropyl group can be linked to any carbon atom on the pyridine ring;

In yet other aspects, the disclosed R-ODH methods and catalysts also may pertain to one or more of the following: R-ODH of 1-butene to 1,3-butadiene; R-ODH of 2-butene to 1,3-butadiene; R-ODH of cyclohexene to benzene; or R-ODH of 1-hexene to 1,3,5-hexatriene. One having ordinary skill in the art, having reviewed the disclosure herein, would understand how to use and or adapt the various aspects described herein to these and other R-ODH reactions.

C. Catalyst

In an aspect, the disclosure relates to a redox catalyst for redox oxidative dehydrogenation (R-ODH), such as the R-ODH of alkane aromatic hydrocarbons. The disclosed redox catalysts combine catalytic dehydrogenation (DH) activity and selective hydrogen combustion (SHC) functions. In other words, the disclosed redox catalysts comprise a dehydrogenation component for the conversion of dehydrogenation reactants to dehydrogenated reaction products and oxygen storage material for selective hydrogen combustion during the dehydrogenation. In certain aspects, the redox catalyst possesses the functions of both catalytic dehydrogenation and hydrogen selective combustion. The redox catalyst comprises catalytic dehydrogenation components and oxygen storage components, as described further herein. In some aspects, the catalytic dehydrogenation and hydrogen selective combustion components may independently comprise the same materials, or different materials. For example, the catalytic dehydrogenation and hydrogen selective combustion components may comprise the same metal oxides particle, or mixed metal oxides particles, or independent metal oxides particles.

In some aspects, the catalytic dehydrogenation component comprises one or more of: (i) potassium iron oxides ((K—Fe—O, $K_2O/MeFe_2O_4$ (where Me=Mn, Cu, Co, Zn, or Ni), $K_2O/Ca_2Fe_2O_5$, potassium-modified minerals, and the like); (ii) lithium iron oxide (Li—Fe—O, $Li_2O/MeFe_2O_4$ (where Me=Mn, Cu, Co, Zn, or Ni), $Li_2O/Ca_2Fe_2O_5$, lithium-modified minerals, and the like); (iii) sodium iron oxide ((Na—Fe—O, $Na_2O/MeFe_2O_4$ (where Me=Mn, Cu, Co, Zn, or Ni), $Na_2O/Ca_2Fe_2O_5$, sodium-modified minerals, and the like); (iv) zinc iron oxide ((Zn—Fe—O, ZnO/$MeFe_2O_4$ (where Me=Mn, Cu, Co, Zn, or Ni), ZnO/$Ca_2Fe_2O_5$, zinc-modified minerals, and the like); (v) vanadium oxides ($V_2O_5$/MgO, $V_2O_5$/$TiO_2$—$ZrO_2$, $V_2O_5$/$CeO_2$—$ZrO_2$, vanadium-rich minerals, and the like); or any combination thereof.

In some aspects, the composition of the dehydrogenation (DH) component in the redox catalyst may be selected according to the dehydrogenation catalysts in recent industry or designed on the basis of active sites for dehydrogenation. For example, K—Fe—O and $V_2O_5$ are the active components in the typical industrial dehydrogenation catalyst. In addition, other metal oxides are also effective for the dehydrogenation of alkyl aromatic compounds (i.e. Ce—$ZrO_2$, $U_2O_3$, $MoO_3$, Bi and/or Mo containing complex oxides, etc.).

In some aspects, the hydrogen selective combustion component comprises one or more of: (i) iron-containing oxides ($Fe_2O_3$, $Fe_3O_4$, $MnFe_2O_4$, $CuFe_2O_4$, iron-rich minerals, and the like); (ii) vanadium oxides or vanadium-rich minerals; (iii) bismuth molybdate or molybdenum oxide; (iv) perovskite oxides or oxides belonging to the perovskite structure family, including but not limit to those represented by: $ABO_3$, $A_2B_2O_5$, and/or $A_{n+1}BnO_{3n+1}$, wherein A may be Ca, Sr, Ba, La, and/or other lanthanides, B may be a transition metal (Mn, Fe, Co, and the like), and the A-site or B-site may be partially substituted by one or more of rare metals, transition metal, alkali metals, and alkaline-earth metals; and/or (v) cerium oxides ($CeO_2$, $CeO_2$—$SmO_2$, $CeO_2$—$ZrO_2$, and the like); or any combination thereof.

In some aspects, the hydrogen selective combustion component may be further modified by a modification agent to enhance the performance of selective hydrogen combustion. Exemplary modification agents include carbonate, alkali metal oxide/salts, sulfates, phosphates, molybdates, or tungstate. In some aspects, the modification agent comprises alkali and/or alkali earth oxides, carbonates, phosphates, pyrophosphates, tungstates, sulfates, molybdates or combinations or mixtures thereof. In some aspects, the modification agent comprises a dispersion comprising more than one modification agent. In some aspects, the dispersion further comprises a molten salt. The molten salt can be used to enhance the dispersion of the modification agents on the redox catalyst.

Figure 5:
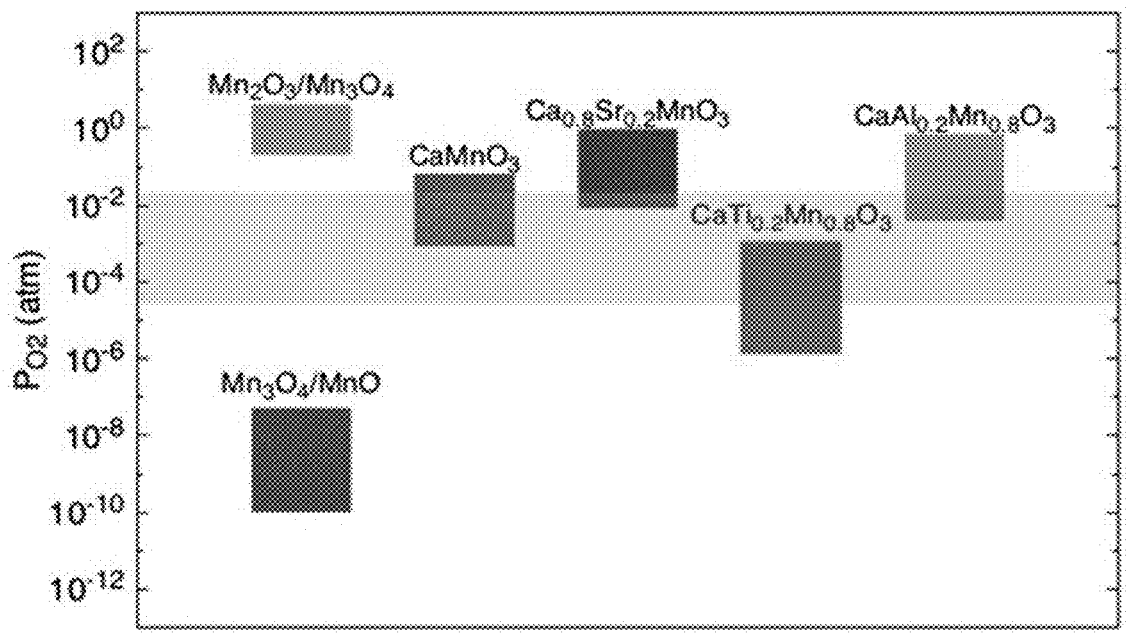
FIG. 5 shows the partial oxygen pressure ($P_{O2}$) for the redox pairs when metal oxides are used as the oxygen storage materials according to aspects of the present disclosure. $P_{O2}$ in the reaction of $MeO_x \rightarrow Me_{x-y} + y/2 O_2$, can be used to evaluate the oxygen releasing ability at the specific temperature.

In an aspect, the design of redox catalysts can be such that the oxygen storage material used as selective hydrogen combustion (SHC) component can be tailored based on its oxygen release properties to simplify the heat management of the process. For a given class of mixed oxide oxygen carriers e.g. doped $Ca_xA_{1-x}Mn_yB_{1-y}O_{3-\delta}$ (A=Sr, Ba, La, K or other lanthanides or alkali metal cations or mixture thereof; B=Fe, Mg, Cu, Ti, Cr, V, Mo, Ce, Zr, or mixture thereof), the strength of the metal oxygen bonds, oxygen vacancy formation energy, and oxygen release properties such as oxygen capacity, rate, and equilibrium oxygen partial pressure can be modified by varying the dopant composition (x and y in $Ca_xA_{1-x}Mn_yB_{1-y}O_{3-\delta}$) and dopant types as illustrated in FIG. 5. While $Ca_xA_{1-x}Mn_yB_{1-y}O_{3-\delta}$ is given as an example, it will be understood that this principle generally applies to other mixed oxide SHC/oxygen storage materials of perovskite and perovskite related structures (e.g. Ruddlesden-Popper, Brownmillerite, Aurivillius, and Dion-Jacobson phases), mixed oxides containing one more of the following cations including Fe, Co, Mn, Ni, and Cu. By modifying the oxygen release properties of the mixed oxide, the heat of reaction for the alkyl aromatic R-ODH reaction (e.g. $yC_8H_{10}+MeO_x \rightarrow yC_8H_8+yH_2O+MeO_{x-y}$) can also be modified. In general, higher equilibrium oxygen partial pressure corresponds to weaker metal oxygen bonding and higher heat of reaction. As such, the heat of reaction for the R-ODH step can be tuned from highly endothermic to slightly exothermic. Without losing the generality, the following sample reactions show the degree of tunability for the heat of reactions:

R-ODH Step: $C_8H_{10}+2MnO_2 = C_8H_8+Mn_2O_3+H_2O$ ($\Delta H \approx -38$ kJ/mol at 600° C.)

Re-oxidation Step: $Mn_2O_3+\frac{1}{2}O_2 = 2MnO_2$ ($\Delta H \approx -84$ kJ/mol at 600° C.)

R-ODH Step: $C_8H_{10}+Mn_3O_4 = C_8H_8+3MnO+H_2O$ ($\Delta H \approx 108$ kJ/mol at 600° C.)

Re-oxidation Step: $3MnO+\frac{1}{2}O_2 = Mn_3O_4$ ($\Delta H \approx -229$ kJ/mol at 600° C.)

As can be seen from the above, the heat of reaction for the R-ODH step can be adjusted by varying the metal oxide redox catalyst pair ($MnO_2/Mn_2O_3$ vs. $Mn_3O_4/MnO$ in the above example) and the oxidation state and/or coordination environment of the transition metal cation, which is responsible for oxygen storage and release (Mn cation in this case, other examples include the cations of Fe, Mn, Co, Ni, Cu, V, Mo, Bi, Ce, etc.). While the overall heat of reaction for the R-ODH step and the Re-oxidation step added together is the same, tailored redox catalyst redox pairs that allow near heat neutral or exothermic R-ODH step can allow easier heat integration.

From a selectivity enhancement standpoint, one or more dopants may be intentionally added to a mixed oxide to change the oxidation state and hence to limit (or increase) the loosely bonded, non-selective oxygen species in the redox catalyst. For example, in the case of $Ca_xA_{1-x}Mn_yB_{1-y}O_{3-\delta}$, addition of $La^{3+}$ as the A-site dopant ($A_{1-x}$) could lower the oxidation state of the B-site cation ($Mn^{n+}$) and hence can lower the amount of nonselective oxygen species. Other dopants include Sr, Ba, La, K or other lanthanides or alkali metal cations or mixture thereof for A and Fe, Mg, Cu, Ti, Cr, V, Mo, Ce, Zr, or mixture thereof for B. While $Ca_xA_{1-x}Mn_yB_{1-y}O_{3-\delta}$ serves as a general example, other Mn, Fe, Ni, Co, Cu containing perovskite and perovskite related mixed oxides as well as spinel, fluorite, bixbyite, or hexaaluminate structured mixed oxides can also exhibit similar oxygen storage and/or SHC properties. In addition, promoting the mixed oxide with alkali or alkali-earth metal containing oxides or salts such as alkali/alkali earth tungstate, alkali phosphate, alkali sulfates, alkali halides, alkali carbonates or mixture thereof can further increase the selectivity of these mixed oxide based oxygen carrier's selectivity for hydrogen combustion. The promotion can be performed via impregnation of the corresponding salts or oxide precursors onto the pre-synthesized oxides. In another embodiment, the oxide can be synthesized along with the promoters via a one pot approach.

In various aspects, the molar ratio of catalytic dehydrogenation component to hydrogen selective combustion component can vary from 10:0 to 0:10, such as, for example from about 9:1, to about 1:9, from about 8:2 to about 2:8, from about 7:3 to about 3:7, from about 6:4 to about 4:6; or about 5:5. The molar ratio of catalytic dehydrogenation component to hydrogen selective combustion component can be any effective ratio, so long as the hydrogen resulting from dehydrogenation step can be timely and selectively combusted in the selective hydrogen combustion step, according to the disclosed methods.

According to the various aspects these two functionalities (DH, SHC) can be combined into the same redox catalyst on a single active site or spatially adjacent active sites (at atomistic scales) or on spatially separated active sites. Alternatively, two distinct sets of catalysts with distinct DH and SHC functions can be physically integrated to achieve the above-described functionality. FIGS. 1A-1B illustrate different strategies to design the redox catalysts to achieve the abovementioned SHC and DH functions. For example, referring to FIG. 1A, in one aspect, particles of DH catalytic material and particles of oxygen storage material can be directly mixed together via physical mixing or related methods such as solid state mixing, slurry mixing, freeze granulation, or spraying drying to form a redox catalyst having active sites for DH and for SCH. Alternatively, particles of DH catalytic material and particles of oxygen storage material can be placed in a packed bed reactor to form multiple layers (layer by layer), each layer having a specified functionality. Referring to FIG. 1B, in another aspect, the DH and SHC functionalities of the disclosed redox catalyst are achieved on a single or spatially adjacent active sites or spatially separated active sites at a single particle and/or atomistic scales. To achieve such functionalities, one can form a core-shell structure with the core being a lattice oxygen storing oxide material and the shell being an active catalyst for both DH and SHC to achieve conversion of alkyl aromatics to their unsaturated counterparts and water. In yet another catalyst design strategy, the active catalyst component does not fully cover the oxygen storage material. Under such a configuration, the active catalyst has, at minimum, the DH functionality but can also be active for SHC. The surface of the exposed oxygen storage material acts either as an inert or a surface that is substantially more active for hydrogen combustion when compared to C—H or C—C bond activation. The lattice oxygen storage capacity of the redox catalysts varies from 0.5 to 30 wt. %. Both the oxygen storage capacity and dehydrogenation activity of the redox catalyst may be tuned by changing its structure, composition, and/or surface properties. In another aspect, the redox catalyst comprises a bifunctional component, in other words, the component comprises a material having both functions.

In an aspect, the disclosed redox catalyst can comprise a potassium modified iron oxide combined with an iron-based SHC component. For example, the redox catalyst can comprise $K_2O/MnFe_2O_4$, where the catalytic dehydrogenation component is $K_2O$—$FeO_x$ and the selective combustion component comprises $MnFe_2O_4$. In an aspect, $MnFe_2O_4$ can be synthesized first via a co-precipitation, sol-gel, solution combustion, hydrothermal, or solid state reaction method. Precursors for $MnFe_2O_4$ are metal salts, alkoxides, and/or metal oxides. It is then sintered at 650° C. to 1200° C. to allow phase formation. Potassium precursor is then incorporated into the as-synthesized oxygen storage material by wet-impregnation method. Precursors (potassium nitrate or other K-containing salts) for $K_2O$ are dissolved in one solution and impregnated onto $MnFe_2O_4$. The $K_2O$ loading of the catalyst can range from about 1 wt % to about 10 wt % or from about 2 wt % to about 9 wt % or from about 3 wt % to about 7 wt % or from about 4 wt % to about 6 wt % or about 5 wt %. It is then sintered again at 650° C. to 1200° C. to form the desired K—Fe—O phases on the surface.

In an aspect, the disclosed redox catalyst can comprise a potassium iron oxide catalytic dehydrogenation component combined with oxygen storage material such as, for example, $CaMnO_3$. In an aspect, the $CaMnO_3$ can be synthesized first via a co-precipitation, sol-gel, solution combustion, hydrothermal, or solid state reaction method. Precursors include metal salts, alkoxides, and/or metal oxides. It is then sintered at 650° C. to 1200° C. to allow phase formation. Catalytic material such as K—Fe—O mixed oxide (Potassium iron oxides) is then constructed on the as-synthesized oxygen storage material. Precursors for K—Fe—O are dissolved in one solution and impregnated onto $CaMnO_3$. In various aspects, the K—Fe—O loadings in the redox catalyst may be from about 20 wt % to about 60 wt %, or from about 25 wt % to about 55 wt % or from about 30 wt % to about 50 wt %, or from about 35 wt % to about 45 wt %, on the basis of the total weight of the redox catalyst. It is then sintered again at 650° C. to 1200° C. to form the desired phases for the redox catalyst.

In an aspect, the disclosed redox catalyst can comprise a vanadium oxide. Vanadium oxide has dual-functional roles for catalysis of dehydrogenation and oxygen storage. In other words, the redox catalyst can comprise $V_2O_5$ as the oxygen storage material as well as a DH catalyst. In an aspect, the $V_2O_5$/MgO can be a commercially-available product or synthesized via co-precipitation method or a solid-state method. Precursors for $V_2O_5$/MgO include nitrate salts or metal oxides. It is then sintered at 600° C.-650° C. to allow phase formation. In some aspects, one or more other oxygen storage materials may be used as supports instead of MgO in vanadium oxides. In various aspects, the $V_2O_5$ loading in the redox catalyst can be from about 2 wt % to about 80 wt %, or from about 4 wt % to about 78 wt %, or from about 6 wt % to about 76 wt %, or from about 8 wt % to about 74 wt % or from about 10 wt % to about 72 wt %, or from about 10 wt % to about 70 wt %, or from about 15 wt % to about 65 wt % or from about 20 wt % to about 60 wt %, or from about 25 wt % to about 55 wt %, or from about 30 wt % to about 50 wt %, or from about 35 wt % to about 45 wt %, on the basis of the total weight of the redox catalyst.

In an aspect, the redox catalyst can comprise a direct mixture of the DH catalyst component and the SHC/oxygen storage component. For example, $KFeO_2$—$La_{0.6}Sr_{1.4}FeO_4$ mixed oxide may be synthesized by co-precipitation method or a sol-gel method using nitrate salts as precursors. It is then sintered at 800° C.-1300° C. to allow desirable phase formation. $CaMnO_3$ in $Na_2WO_4$—$CaMnO_3$, is provided as the oxygen storage material, which may be first synthesized by co-precipitation method or a sol-gel method and then impregnated in a $Na_2WO_4$ solution. The obtained mixture of $Na_2WO_4$-impregnated $CaMnO_3$ may be sintered at 650° C.-1300° C. to prepare the desired oxygen storage material. $KFeO_2$—$La_{0.6}Sr_{1.4}FeO_4$ and $Na_2WO_4$—$CaMnO_3$ may be mixed according to a weight ratio ranging from 9:1 to 1:9, or from about 8.5:1.5 to about 1.5:8.5, or from about 8:2 to about 2:8, or from about 7.5:2.5 to about 2.5:7.5, or from about 7:3 to about 3:7, or from about 6.5:3.5 to about 3.5:6.5, or from about 6:4 to about 4:6, or from about 5.5:4.5 to about 4.5:5.5 or about 5:5.

D. Methods

In another aspect, the disclosure relates to a process for redox oxidative dehydrogenation of one or more dehydrogenation reactants. According to the various aspects, the disclosed process involves the use of one or more of the disclosed redox catalysts.

According to the various aspects, one or more dehydrogenation reactants is introduced to or combined with the disclosed redox catalyst, and dehydrogenated to produce a corresponding dehydrogenation product and hydrogen. Exemplary dehydrogenation reactants comprise an alkyl aromatic hydrocarbon or a substituted alkyl aromatic hydrocarbon and the dehydrogenated reaction product comprises an alkene aromatic hydrocarbon or substituted alkene aromatic hydrocarbon, respectively. Other exemplary dehydrogenation reactants comprise an alkyl naphthalene and the dehydrogenated reaction product comprises an alkene naphthalene. Yet other exemplary dehydrogenation reactants comprise an alkyl furan, alkyl pyrrole, alkyl thiophene, or alkyl pyridine, and the dehydrogenated product comprises alkene furan, alkene pyrrole, alkene thiophene, or alkene pyridine, respectively. Other exemplary dehydrogenation reactants comprise a 1-butene or 2-butene, and the dehydrogenation product comprises 1,3-butadiene.

According to an aspect, the disclosed method includes a step of catalytically converting the one or more dehydrogenation reactants to a corresponding dehydrogenation product through dehydrogenation. In a reduction step, one or more C—C bonds of the dehydrogenation reactants may be selectively converted into double or triple bonds by using specifically-designed redox catalysts. In the dehydrogenation step, a metal or metal oxide catalyst having dehydrogenation (DH) activity is used, as described herein.

The disclosed method further includes selectively combusting the hydrogen released during dehydrogenation using a lattice oxygen from the metal oxide catalyst thereby reducing the metal oxide catalyst.

FIGS. 1A and 1B illustrate the DH/SHC step of the R-ODH process (as illustrated with R-ODH of ethylbenzene to styrene) for some exemplary redox catalyst structures. In the figures, light colors correspond to dehydrogenation (DH) component and dark colors correspond to selective hydrogen combustion (SHC) component, respectively. In the core-shell illustration case (FIG. 1B), the darker color also corresponds to materials that are bifunctional (DH+SHC).

The disclosed method conducts R-ODH at high temperature, e.g., temperature from about 400° C. to 700° C. In the reduction step, C—C bond in the alkane attached to benzene ring is catalytically dehydrogenated while the hydrogen produced from this dehydrogenation is selectively combusted to water by redox catalyst. To prevent over-reduction of the redox catalysts and ensure the conversion of hydrogen from dehydrogenation, which may cause coke formation and catalyst deactivation, the method includes a suitable gas-solid contact time, such as, for example, from about 0.1 second to 120 seconds.

According to an aspect, the disclosed method further includes re-oxidizing the reduced metal oxide catalyst by introducing a gaseous oxidant to the reduced metal oxide catalyst. The lattice oxygen-deprived redox catalyst can be re-oxidized using any oxidant. Exemplary oxidants include air, oxygen, water, $CO_2$, and any mixture thereof.

In the oxidation step for the regeneration of redox catalyst, a full oxidation can be conducted to replenish the redox catalyst. In some aspects, the regeneration degree of redox catalyst may be controlled by partial regeneration, oxidation with dilute oxygen, use of soft oxidants (e.g., $CO_2$ or $H_2O$), and/or pulse of the oxidants to avoid over-reoxidization and non-selective oxygen formation in redox catalyst.

According to an aspect, the disclosed method further optionally includes re-using the re-oxidized metal oxide catalyst for one or more of dehydrogenation and/or selective combustion.

In some aspects, the method involves cyclic redox. In the cyclic redox of R-ODH, the reduction and oxidation steps are alternately conducted for the efficient dehydrogenation as well as hydrogen selective combustion. The steps may be repeated in iterations, such as two or more iterations, or three or more iterations, or four or more iterations.

The disclosed methods, or steps thereof, can be performed in any suitable reactor. Suitable reactor configurations include fluid bed, fixed bed, moving bed, simulated moving bed, or rotating bed reactors. One having ordinary skill in the art would recognize these and other reactor designs suitable for performing the disclosed methods, or portions thereof. According to some aspects, the disclosed methods are performed in two or more reactors in series. For example, the reduction step can be performed in a first reactor, and the oxidation step can be performed in a second reactor. According to various aspects, any one of the reactors in the disclosed R-ODH process or apparatus can be further configured to include multiple packed bed reactors in parallel. According to various aspects, any one of the reactors in the disclosed R-ODH process or apparatus can be further be configured to include multiple layers of catalysts with varying compositions, functionality, or a combination thereof.

According to various aspects, heat management in the R-ODH step may be regulated at least in part by the design of the redox catalyst, as discussed herein, for improved heat integration and/or simplified reactor design.

The catalytic dehydrogenation and hydrogen selective combustion can take place either sequentially or simultaneously in the temperature range of 350-750° C. Since the selective oxidation reaction removes the hydrogen from the dehydrogenation process in a timely manner, the thermodynamic equilibrium limitation is greatly eliminated. The heat from selective hydrogen combustion neutralizes the energy consumption in dehydrogenation, resulting in more efficient energy utilization. Moreover, the process does not require co-feeding gaseous oxygen with the alkyl aromatic feedstock. Usage of externally added steam can also be reduced or eliminated. Several families of redox catalysts with bifunctional designs and their applications for R-ODH are described herein.

Figure 6:
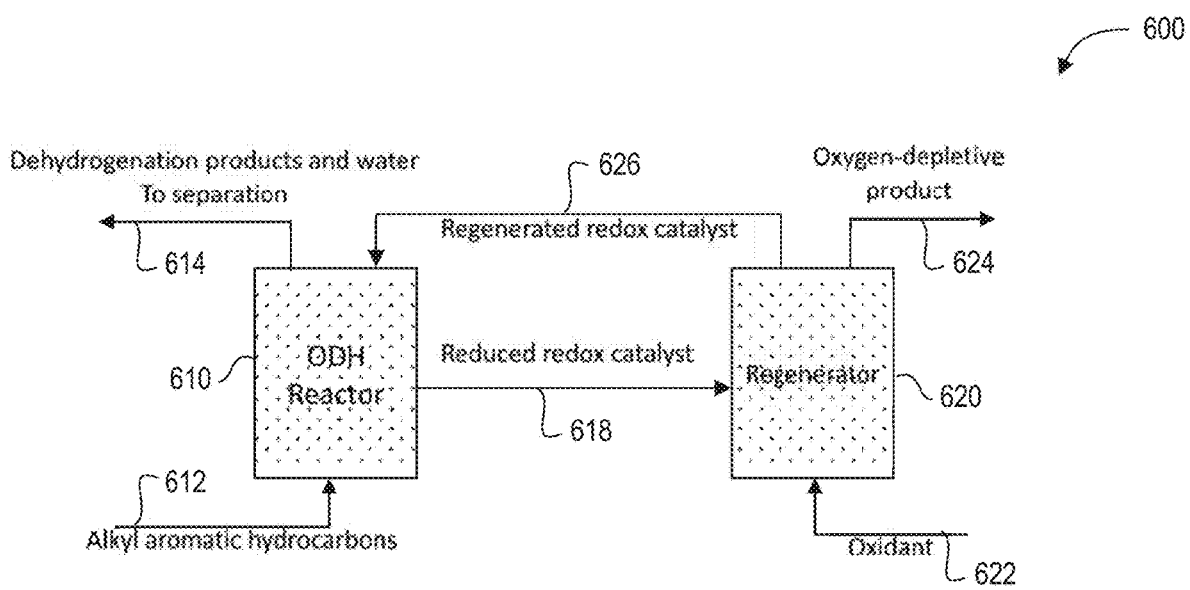
FIG. 6 shows an exemplary circulating fluidized bed system for R-ODH, according to aspects of the present disclosure.

Using the redox catalysts and R-ODH scheme described above, R-ODH can be conducted with a circulating fluidized bed. An exemplary R-ODH scheme according to the various aspects is illustrated in FIG. 6, in which the circulating fluidized bed process 600 includes two major reactors: ODH reactor 610 and regenerator 620 packed with the redox catalyst. The ODH reactor 610 operates at between 350° C. to 700° C. Dehydrogenation reactants 612, such as alkyl aromatic hydrocarbons are introduced to the redox catalysts in the ODH reactor 610, and are catalytically converted into dehydrogenated reaction products, such as alkene aromatic hydrocarbons, and hydrogen. The hydrogen produced in the ODH reaction can be selectively combusted by the redox catalyst, providing additional heat to the reactor. As a result, the ODH reactor produces dehydrogenated products and water 614, which may then be transported and separated. The resulting reduced redox catalysts 618 can then be pneumatically and/or mechanically transported to the regenerator 620. At regenerator 620, an oxidant 622 such as air or other suitable oxidizing gas such as $CO_2$ or steam is introduced to catalysts, replenishing the redox catalyst's oxygen. As a result, the regenerator 620 produces regenerated redox catalyst 626, and an oxygen depletive product 624. The regenerated redox catalyst 626 can then be pneumatically and/or mechanically transported to the ODH reactor 610.

Figure 7:
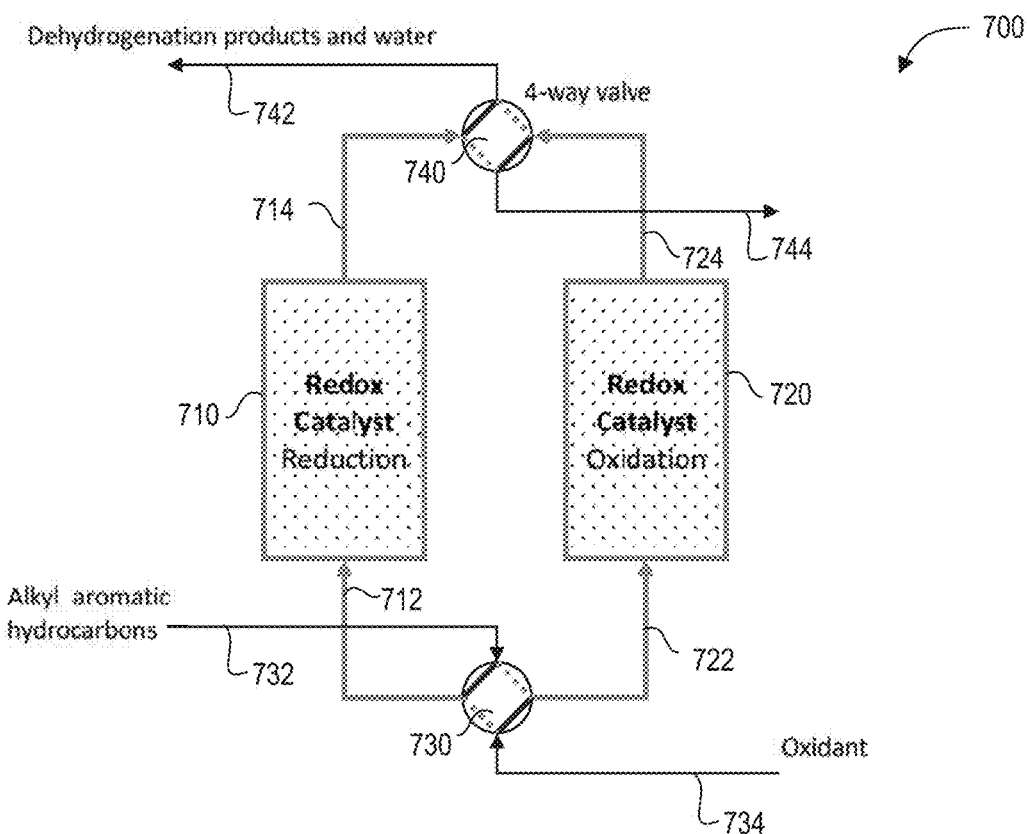
FIG. 7 shows an exemplary system of fixed-bed reactors according to aspects of the present disclosure.

An alternative R-ODH system according to the various aspects is illustrated in FIG. 7, in which a continuous or semi-continuous circulating fluidized bed process 700 comprises two alternately recycled fixed-bed reactors 710 and 720 packed with the redox catalyst. Generally speaking, in this aspect, rather than moving the reduced and regenerated redox catalysts between reactors, the reactants for each of the steps are alternately fed to one or the other reactor 710 and 720, resulting in alternating oxidation and reduction reactions in each reactor 710 and 720. Referring to FIG. 7, first fixed bed reactor 710 has a first inlet 712 and a first outlet 714; and second fixed bed reactor 720 has a second inlet 722 and a second outlet 724. The fluidized bed process 700 further comprises a first inlet 4-way valve 730, which is in fluid communication with first inlet 712 and second inlet 722. First inlet 4-way valve 730 also is in fluid communication with a first reactant stream 732 comprising dehydrogenation reactants, and a second reactant stream 734 comprising oxidants. The first inlet 4-way valve 730 is configured to transition between at least a first position (illustrated with solid lines), and a second position (illustrated with dashed lines). In the first position, the first inlet 4-way valve 730 provides fluid communication between the first reactant stream 732 and the first inlet 712, and provides fluid communication between the second reactant stream 734 and the second inlet stream 722. When the first inlet 4-way valve 730 is in the first position, the dehydrogenation reactants in the first reactant stream 732 are introduced to the redox catalysts in the first reactor 710, and are catalytically converted into dehydrogenated products and hydrogen. The hydrogen produced in the ODH reaction can be selectively combusted by the redox catalyst, providing additional heat to the reactor. As a result, the ODH reactor produces dehydrogenation products and water which can exit the first reactor 710 at first outlet 714. As a result of the reduction reaction, the redox catalysts in first reactor 710 will be in a reduced state. Simultaneously, when the first inlet 4-way valve 730 is in the first position, the oxidants in the second reactant stream 734 are introduced to the (reduced) redox catalysts in the second reactor 720, oxidizing the redox catalysts. As a result of the oxidation reaction, the redox catalysts are in a regenerated state, having their oxygen replenished, and an oxygen-depleted reaction product is produced, which can exit second reactor 720 at second outlet 724.

In the second position, the first inlet 4-way valve 730 provides fluid communication between the first reactant stream 732 and the second inlet 722, and provides fluid communication between the second reactant stream 734 and the first inlet stream 712. When the first inlet 4-way valve 730 is in the second position, the dehydrogenation reactants in the first reactant stream 732 are introduced to the (regenerated) redox catalysts in the second reactor 720, and are catalytically converted into dehydrogenated products and hydrogen. The hydrogen produced in the ODH reaction can be selectively combusted by the redox catalyst, providing additional heat to the reactor. As a result, the ODH reactor produces dehydrogenation products and water which can exit the second reactor 720 at second outlet 724. As a result of the reduction reaction, the redox catalysts in second reactor 720 will be in a reduced state. Simultaneously, when the first inlet 4-way valve 730 is in the second position, the oxidants in the second reactant stream 734 are introduced to the (reduced) redox catalysts in the first reactor 710, oxidizing the (reduced) redox catalysts therein. As a result of the oxidation reaction, the redox catalysts are in a regenerated state, having their oxygen replenished, and an oxygen-depleted reaction product is produced, which can exit first reactor 710 at first outlet 714.

Still referring to FIG. 7, the fluidized bed process 700 may also include a second outlet 4-way valve 740. The second outlet 4-way valve 740 is in fluid communication with the first outlet 714 and second outlet 724. The second outlet 4-way valve 740 also is in fluid communication with a first fluid conduit 742 that transports dehydrogenation products and water, for example for further downstream separation and/or processing. The second outlet 4-way valve 740 also is in fluid communication with a second fluid conduit 744 that transports oxygen-depleted reaction products produced in the oxidation reactions, for example for further downstream processing. The second outlet 4-way valve 740 is configured to transition between a first position (illustrated with solid lines), and a second position (illustrated with dashed lines). In the first position, the second outlet 4-way valve 740 provides fluid communication between the first outlet 714 and the first fluid conduit 742, so that the dehydrogenation products and water are transported from the first reactor 710 to the first fluid conduit 742. In the first position, the second outlet 4-way valve 740 provides fluid communication between the second outlet 724 and the second fluid conduit 744, so that the oxygen-depleted reaction products are transported from the second reactor 720 to the second fluid conduit 744. In the second position, the second outlet 4-way valve 740 provides fluid communication between the second outlet 724 and the first fluid conduit 742, and provides fluid communication between the first outlet 714 and the second fluid conduit 744.

In an aspect, the fluidized bed process 700 is operated so that in a first step, the first inlet 4-way valve 730 and the second outlet 4-way valve 740 are in their respective first positions, so that the reactants in first reactor 710 undergo the ODH reaction, and the reactants in the second reactor 720 undergo an oxidation reaction (regenerating the redox catalyst therein); and in a second step the first inlet 4-way valve 730 and the second outlet 4-way valve 740 are in their respective second positions, so that the reactants in the first reactor 710 undergo an oxidation reaction (regenerating the redox catalyst), and the reactants in the second reactor 720 undergo the ODH reaction. By managing and controlling the inlet streams and outlet streams with the 4-way valves 730 and 740, the process 700 may be operated continuously or semi-continuously, enabling continuous input of dehydrogenation reactants and oxidant as well as the continuous output of dehydrogenation products.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

In an aspect, an inert heat transport carrier may be cycled with the oxygen carriers so that thermal sufficiency of the reaction can be maintained, even when a lower charged redox catalyst particle or lower circulation rate is employed. Exemplary heat transport carriers include $Al_2O_3$, $ZrO_2$, $TiO_2$, other inert compounds and their corresponding minerals, or any combination thereof. In an aspect, the inert heat transport carrier may be an $\alpha$-$Al_2O_3$ of silicon carbide. In some aspects, the inert heat transport agent exhibits phase transitions allowing for storage of heat beyond the heat capacity of the inert heat transport material itself, enhancing heat transfer and allowing less temperature difference between ODH and redox regeneration temperatures. In some aspects the redox catalyst may be directly mixed with inert heat transport agent or coated on the surface to form combined particles.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. K—Fe—O Redox Catalyst

This example demonstrates the preparation and performance of exemplary redox catalysts comprising a potassium modified iron oxides catalyst. Four exemplary catalysts were prepared and utilized, as detailed in Tables 1, 2 and 3.

One exemplary redox catalyst, $K_2O$/$MnFe_2O_4$ contained a catalytic dehydrogenation component ($K_2O$—$FeO_x$) and a SHC component ($MnFe_2O_4$). Each of the catalysts was synthesized using a sol-gel method, from associated precursors comprising metal salts, alkoxides, and/or metal oxides. It was then sintered at 650° C. to 1200° C. to allow phase formation. Potassium precursor was then incorporated into the as-synthesized oxygen storage material by wet-impregnation method. Precursors (potassium nitrate or other K-containing salts) for $K_2O$ were dissolved in one solution and impregnated onto $MnFe_2O_4$. $K_2O$ loading from 1 wt % and 10 wt % were used. It was then sintered again at 650° C. to 1200° C. to form the desired K—Fe—O phases on the surface.

In this example, the redox catalyst was provided in a packed bed reactor. For R-ODH of ethylbenzene to styrene in the temperature ranging from 550° C. to 650° C., styrene yield from 50% to 95% were achieved in the packed bed reactor, with styrene selectivity ranging from 80% to 95% and conversion from 60% to 100%. Hydrogen species ($H_2$ and/or H-involved intermediate) from dehydrogenation were converted efficiently and provide additional heat to the reaction. The $H_2$ conversions range from 60% to 100%. The conversion and selectivity numbers can be modified by: A) varying the duration of the ODH step (degree of reduction); B) varying the duration of the re-oxidation step (degree of re-oxidation); and/or C) varying the operating temperature, space velocity of ethylbenzene, and/or ethylbenzene concentration. Table 1 shows R-ODH performance of representative redox catalysts at LHSV of 0.2 $h^{-1}$ and 600 to 620° C.

Figure 2A:
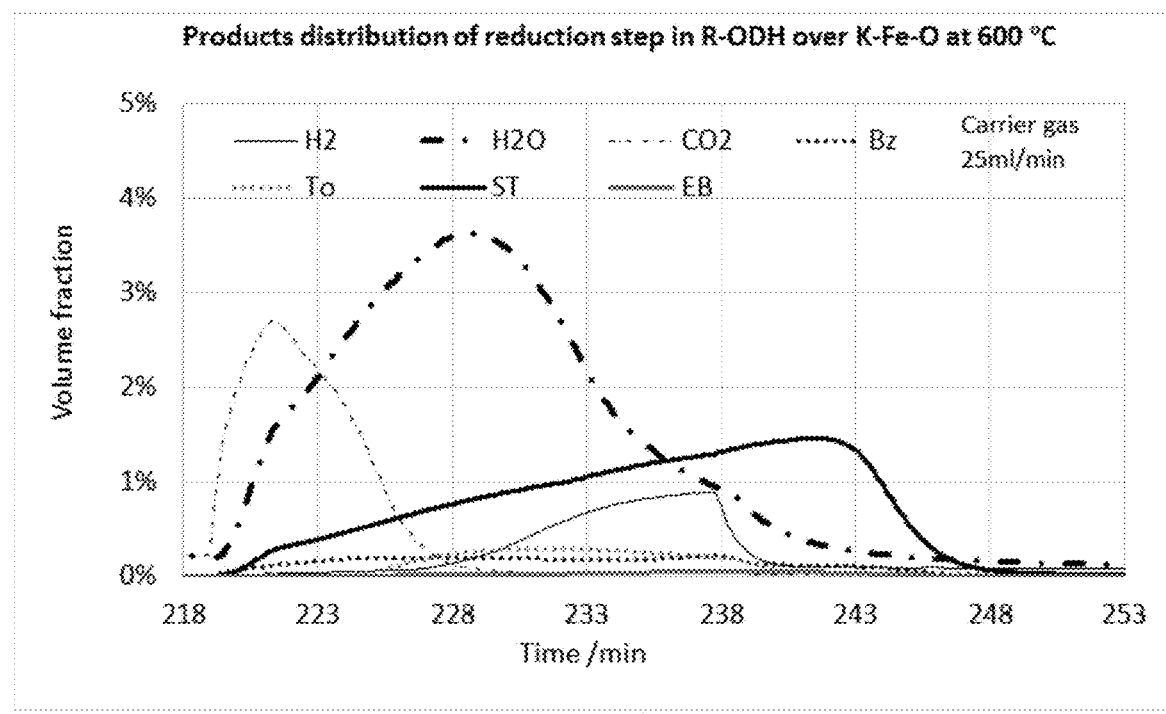
FIGS. 2A-2B shows typical product distribution (FIG. 2A), R-ODH activity (FIG. 2B), and SHC activity in the reduction step of R-ODH over K—Fe—O (7.5 wt % $K_2O$/$Fe_2O_3$) redox catalyst. Reaction condition: 0.5 g of K—Fe—O catalyst was used in the R-ODH at 600° C. The evolved gas was measured by an on line mass spectrometer (MS). The MS signals of ethylbenzene (EB), styrene (ST), toluene (To), and benzene (Bz) were calibrated by a GC.
Figure 2B:
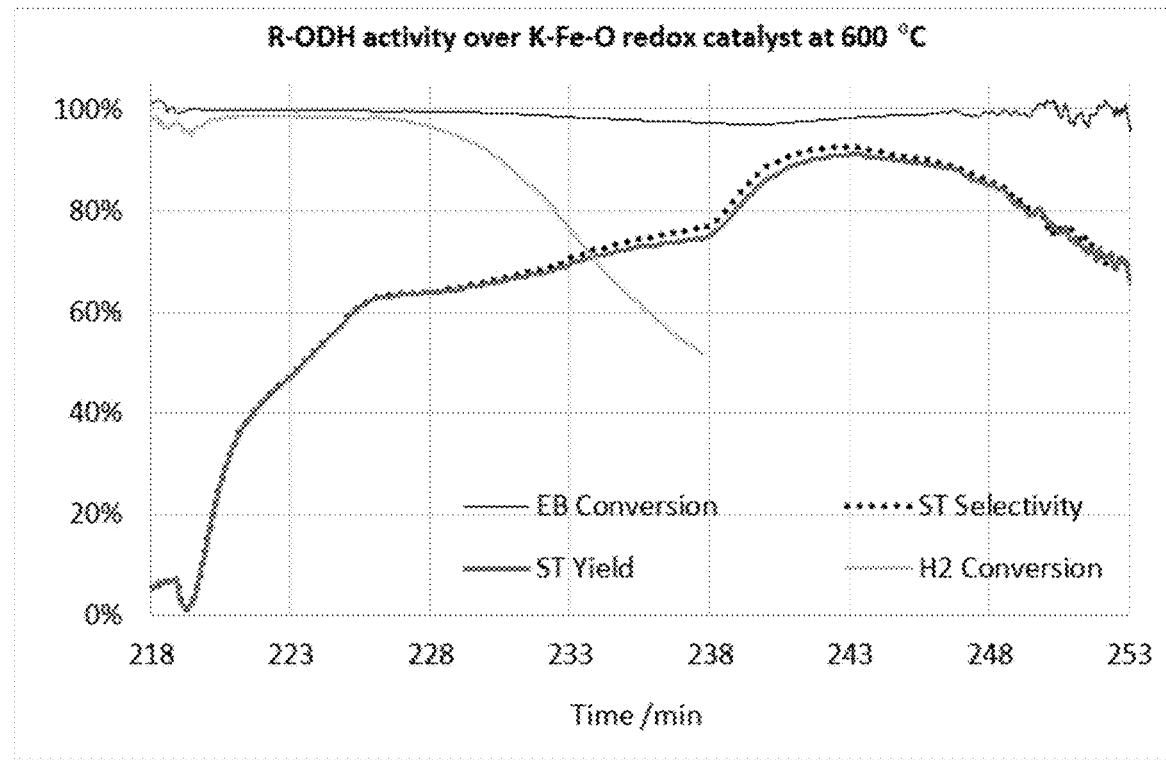

FIGS. 2A-2B show the ethylbenzene R-ODH performance of the 7.5 wt % $K_2O/Fe_2O_3$ redox catalyst. The redox catalyst contained the K—Fe—O and $Fe_2O_3$ phases. It provided high conversion and low styrene selectivity due primarily to the combustion of ethylbenzene to $CO_2$ and $H_2O$. The styrene selectivity increased with the consumption of the oxygen, i.e. decreasing oxidation state of iron. Due to the increase of styrene selectivity, the oxygen selectivity for SHC increased following with the simultaneously selective hydrogen combustion during the ethylbenzene dehydrogenation and hydrogen to water conversion also maintained around 100% in the first 10 minutes. While the hydrogen conversion decreased after the first 10 minutes of the reaction because of the lack of lattice oxygen in the redox catalyst. Moreover, the styrene selectivity was limited to 80% in this case.

Referring to Table 1, it was observed that the K—Fe—O redox catalyst could be further improved by increasing its oxygen storage capacity or tuning its oxidation state. For example, the use of $MnFe_2O_4$ and $CaFe_2O_4$ phases resulted in higher styrene selectivity, near 100% $H_2$ conversion, and improved oxygen storage capacity.

TABLE 1

Performances of potassium iron oxides used for redox catalysts in R-ODH of ethylbenzene.

| Catalyst | Ethylbenzene Conversion | Styrene Selectivity | Styrene Yield | $H_2$ Conversion |
|---|---|---|---|---|
| 7.5 wt % $K_2O/Fe_2O_3$ | 100% | 60-80% | 60-80% | 60-100% |
| 7.5 wt % $K_2O/MnFe_2O_4$ | 100% | 91.8% | 91.8% | ~100% |
| 7.5 wt % $K_2O/CaFe_2O_4$ | 100% | 87.5% | 87.5% | ~100% |

For R-ODH of cumene to α-methylstyrene in the temperature ranging from 350° C. to 650° C., α-methylstyrene yields from 64 to 85% were achieved, with α-methylstyrene selectivity ranging from 80% to 85% and conversion ranging from 80% to 100%. Hydrogen species ($H_2$ and/or H-involved intermediate) from dehydrogenation were converted efficiently and provided additional heat to the reaction. The $H_2$ conversions ranged from 80% to 100%. Table 2 shows the R-ODH performance of exemplary redox catalysts at LHSV of 0.2 $h^{-1}$ and 580 to 600° C.

TABLE 2

Performances of potassium iron oxides used for redox catalysts in R-ODH of cumene.

| Catalyst | Cumene Conversion | α-methylstyrene Selectivity | α-methylstyrene Yield | $H_2$ Conversion |
|---|---|---|---|---|
| 7.5 wt % $K_2O/MnFe_2O_4$ | 80-100% | 80-85% | 64-85% | 100% |
| 7.5 wt % $K_2O/Mn_{0.5}Ni_{0.5}Fe_2O_4$ | 80-100% | 80-85% | 64-85% | 100% |

For R-ODH of 1-butene to 1,3-butadiene in the temperature ranging from 350° C. to 650° C., 1,3-butadiene yields from 30 to 50% were achieved, with 1,3-butadiene selectivity ranging from 80% to 95% and conversion ranging from 20% to 60%. Hydrogen species ($H_2$ and/or H-involved intermediate) from dehydrogenation were converted efficiently and provided additional heat to the reaction. The $H_2$ conversions ranged from 80% to 100%. Table 3 shows the R-ODH performance of exemplary redox catalysts at GHSV of 4000 $h^{-1}$ and 550 to 650° C.

TABLE 3

Performances of potassium iron oxides used for redox catalysts in R-ODH of 1-butene.

| Catalyst | 1-butene Conversion | 1,3-butadiene Selectivity | 1,3-butadiene Yield | $H_2$ Conversion |
|---|---|---|---|---|
| 7.5 wt % $K_2O/MnFe_2O_4$ | 30-50% | 20-60% | 30-50% | 100% |
| 7.5 wt % $K_2O/Mn_{0.5}Ni_{0.5}Fe_2O_4$ | 30-50% | 20-60% | 30-50% | 100% |

2. Perovskite Supported K—Fe—O Redox Catalyst:

This example demonstrates the preparation and performance of an exemplary redox catalyst comprising a potassium modified iron oxides catalyst. Three exemplary catalysts were prepared and evaluated, as detailed in Tables 4 and 5.

Each of the catalysts was synthesized using a sol-gel method, from associated precursors comprising metal salts, alkoxides, and/or metal oxides. It was then sintered at 650° C. to 1200° C. to allow phase formation. Catalytic material such as K—Fe—O mixed oxide (Potassium iron oxides) was then constructed on the as-synthesized oxygen storage material. Precursors for K—Fe—O are dissolved in one solution and impregnated onto $CaMnO_3$. K—Fe—O loadings from 20 wt % and 60 wt % are used. It is then sintered again at 650° C. to 1200° C. to form the desired phases for the redox catalyst.

In this example, the redox catalyst was provided in a packed bed reactor. For R-ODH of ethylbenzene to styrene in the temperature ranging from 550° C. to 650° C., styrene yields from 50%-95% were achieved, with styrene selectivity ranging from 80% to 95% and conversion from 60% to 100%. Hydrogen species ($H_2$ and/or H-involved intermediate) from dehydrogenation were converted efficiently and provided additional heat to the reaction. The $H_2$ conversions ranged from 90% to 100%. Table 4 shows R-ODH performance of three exemplary redox catalysts at LHSV of 0.2 $h^{-1}$ and 600 to 620° C.

The initial $CO_2$ formation could be avoided by partial oxidation of the redox catalyst.

For R-ODH of cumene to α-methylstyrene in the temperature ranging from 500° C. to 600° C., α-methylstyrene yields from 60%-95% were achieved, with α-methylstyrene selectivity ranging from 80% to 90% and conversion from 80% to 100%. Hydrogen species ($H_2$ and/or H-involved intermediate) from dehydrogenation were converted efficiently and provided additional heat to the reaction. The $H_2$ conversions ranged from 90% to 100%. Table 5 shows R-ODH performance of two exemplary redox catalysts at LHSV of 0.2 $h^{-1}$ and 580 to 600° C.

TABLE 5

Performances of perovskite supported K—Fe—O used for redox catalysts in R-ODH of cumene.

| Catalyst | Cumene Conversion | α-methylstyrene Selectivity | α-methylstyrene Yield | $H_2$ Conversion |
|---|---|---|---|---|
| 40 wt % K—Fe—O/$CaMnO_3$ | 80-100% | 85-90% | 69-90% | 100% |
| 40 wt % K—Fe—O/$SrFeO_3$ | 85-100% | 80-90% | 69-90% | 100% |

3. Vanadium Oxide Redox Catalyst:

An exemplary redox catalyst includes a vanadium oxide catalyst. The vanadium oxide has dual-functional roles for catalysis of dehydrogenation and oxygen storage. The exemplary redox catalyst comprises $V_2O_5$ as both oxygen storage material and the DH catalyst. $V_2O_5$/MgO can be a commercial product or synthesized via co-precipitation method or a solid-state method. Precursors for $V_2O_5$/MgO are nitrate salts or metal oxides. It is then sintered at 600° C.-650° C. to allow phase formation. Other oxygen storage material may also be used as supports instead of MgO in vanadium oxides. $V_2O5$ loading from 2 wt % to 80 wt % are used.

For R-ODH of ethylbenzene to styrene in the temperature ranging from 550° C. to 650° C., styrene yields from 50%-95% can be anticipated. The same redox catalyst can be applied for R-ODH of cumene to α-methylstyrene.

TABLE 4

Performances of perovskite supported K—Fe—O used for redox catalysts in R-ODH of ethylbenzene.

| Catalyst | Ethylbenzene Conversion | Styrene Selectivity | Styrene Yield | $H_2$ Conversion |
|---|---|---|---|---|
| 40 wt % K—Fe—O/$CaMnO_3$ | 80-100% | 90-95% | 72-95% | 100% |
| 40 wt % K—Fe—O/$LaMnO_3$ | 80-100% | 85-92% | 69-92% | 100% |
| 40 wt % K—Fe—O/$SrFeO_3$ | 80-100% | 90-94% | 72-94% | 100% |

Figure 3:
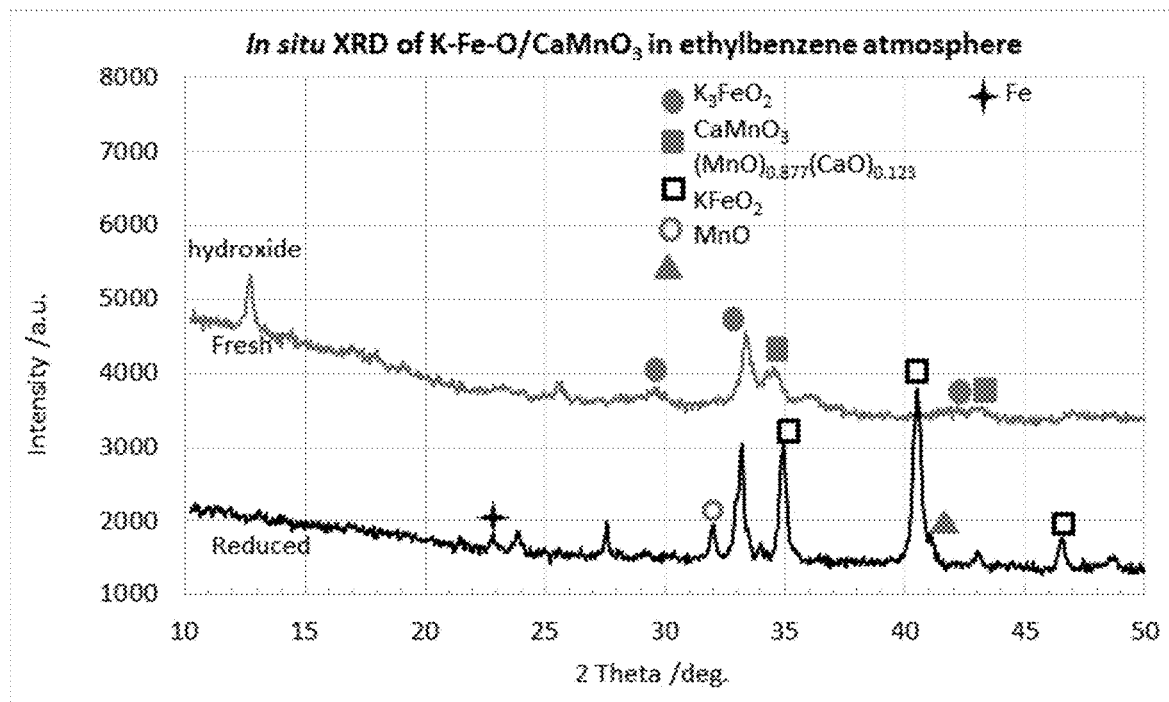
FIG. 3 shows examples of the XRD patterns of K—Fe—O/$CaMnO_3$ redox catalyst obtained from an in situ XRD test according to embodiments of the present disclosure. The fresh sample was scanned at room temperature while the reduced sample was obtained during the ethylbenzene reduction at 600° C.
Figure 4A:
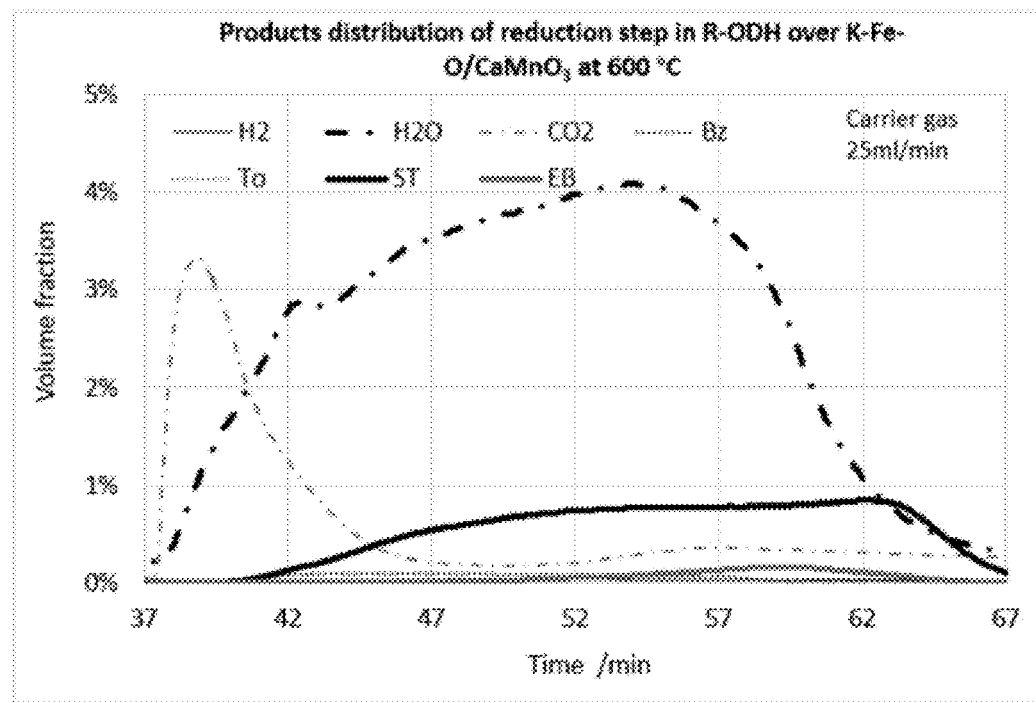
FIGS. 4A-4B show typical products distribution (FIG. 4A), R-ODH activity (FIG. 4B), and SHC activity in the reduction step of R-ODH over K—Fe—O/$CaMnO_3$ redox catalyst according to embodiments of the present disclosure. The evolved gas was measured by an on line mass spectrum. The mass spectrum signals of ethylbenzene (EB), styrene (ST), toluene (To), and benzene (Bz) were calibrated by a GC.
Figure 4B:
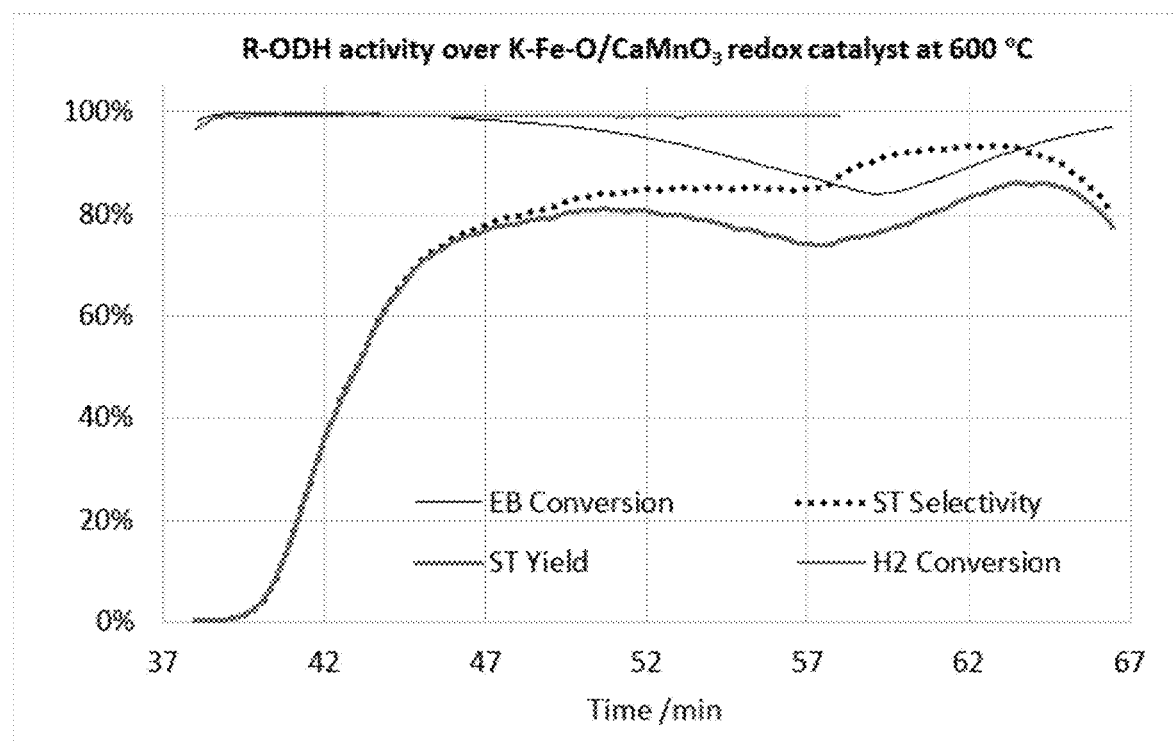

FIG. 3 and FIGS. 4A-4B show in-situ XRD patterns of exemplary K—Fe—O/$CaMnO_3$ redox catalyst in an ethylbenzene atmosphere and its ethylbenzene R-ODH performance at 600° C. The as-prepared redox catalyst comprised $K_3FeO_2$ and $CaMnO_3$. Some iron may have existed as $Fe_2O_3$ in the sample that was not detected by XRD. The reduced sample comprised $(MnO)_{0.877}(CaO)_{0.123}$, MnO, $KFeO_2$, and Fe species. Referring to FIGS. 4A-4B, the ethylbenzene R-ODH performance of K—Fe—O/$CaMnO_3$ redox catalyst shows that the sample successfully maintained a 100% conversion with styrene selectivity in the range of 85-95%. ~100% hydrogen to water. In the beginning of the reduction, the redox catalyst tended to oxidize ethylbenzene to $CO_2$ and $H_2O$. In the following reduction, ethylbenzene was efficiently converted into styrene and water by redox catalyst.

4. Redox Catalysts with Mixture Catalytic and Oxygen Storage Materials:

This example demonstrates the preparation and performance of an exemplary redox catalysts comprising a direct mixture of the DH catalyst component and the SHC/oxygen storage component. Three exemplary catalysts were prepared and evaluated, as detailed in Tables 6 and 7.

In one exemplary redox catalyst, $KFeO_2$—$La_{0.6}Sr_{1.4}FeO_4$ mixed oxide was synthesized by a sol-gel method using nitrate salts as precursors. It was then sintered at 800° C.-1300° C. to allow desirable phase formation. $CaMnO_3$ in $Na_2WO_4$—$CaMnO_3$, was provided as the oxygen storage material, which was first synthesized by a sol-gel method and then impregnated in a $Na_2WO_4$ solution. The obtained mixture of $Na_2WO_4$—impregnated $CaMnO_3$ was sintered at 650° C.-1300° C. to prepare the desired oxygen storage material. $KFeO_2$—$La_{0.6}Sr_{1.4}FeO_4$ and $Na_2WO_4$—$CaMnO_3$ were mixed according to a weight ratio ranging from 9:1 to 1:9.

In this example, the redox catalysts were each provided in a packed bed reactor. For R-ODH of ethylbenzene to styrene in the temperature ranging from 550° C. to 650° C., styrene yielded from 50%-95% was achieved, with styrene selectivity ranging from 80% to 95% and conversion from 60% to 100%. Hydrogen species ($H_2$ and/or H-involved intermediate) from dehydrogenation were converted efficiently and provide additional heat to the reaction. The $H_2$ conversions range from 90% to 100%. Table 6 shows R-ODH performance of the exemplary redox catalysts at LHSV of 0.2 $h^{-1}$ and 620° C.

TABLE 6

Performances of mixture catalytic and oxygen storage materials used for redox catalysts in R-ODH of ethylbenzene.

| Catalyst* | Ethylbenzene Conversion | Styrene Selectivity | Styrene Yield | $H_2$ Conversion |
|---|---|---|---|---|
| $KFeO_2$—$La_{0.6}Sr_{1.4}FeO_4$ and $Na_2WO_4$—$CaMnO_3$ | 80-100% | 80-93% | 64-93% | 100% |
| $KFeO_2$—$ZrO_2$ and $Li_2WO_4$—$CaMnO_3$ | 80-100% | 80-90% | 64-90% | 100% |
| $V_2O_5$—$MgO$ and $SrWO_4$—$MnFe_2O_4$ | 80-100% | 80-90% | 64-90% | 100% |

*The weight ratio of catalytic and oxygen storage materials in redox catalyst equals to 50 wt %.

For R-ODH of cumene to α-methylstyrene in the temperature ranging from 500° C. to 600° C., α-methylstyrene yielded from 60% to 95% were achieved, with α-methylstyrene selectivity ranging from 80% to 95% and conversion from 75% to 100%. Hydrogen species ($H_2$ and/or H-involved intermediate) from dehydrogenation were converted efficiently and provided additional heat to the reaction. The $H_2$ conversions range from 90% to 100%. Table 7 shows R-ODH performance of two exemplary redox catalysts at LHSV of 0.2 $h^{-1}$ and 580 to 600° C.

TABLE 7

Performances of mixture catalytic and oxygen storage materials used for redox catalysts in R-ODH of cumene.

| Catalyst | Cumene Conversion | α-methylstyrene Selectivity | α-methylstyrene Yield | $H_2$ Conversion |
|---|---|---|---|---|
| $KFeO_2$—$La_{0.6}Sr_{1.4}FeO_4$ and $Na_2WO_4$—$CaMnO_3$ mixture | 80-100% | 80-90% | 64-90% | 100% |
| $KFeO_2$—$ZrO_2$ and $Li_2WO_4$—$CaMnO_3$ mixture | 80-100% | 80-90%% | 64-90% | 100% |

In practice, reaction conditions including pressure, temperature, space velocity, contact time, and reduction degree of redox catalyst affect the R-ODH performance. A lower reaction temperature is thermodynamically favorable to avoid cracking and formation of byproducts. In the reduction step, the reduction time should be controlled to obtain a suitable reduction degree and depress possible formation of coke.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A process for producing olefinic compounds, comprising:
   a. introducing one or more dehydrogenation reactants to a metal oxide catalyst having dehydrogenation activity, and dehydrogenating the one or more dehydrogenation reactants to provide an olefinic compound and hydrogen;
   b. selectively combusting at least 50% of the hydrogen released during dehydrogenation using a lattice oxygen from the metal oxide catalyst, resulting in a reduced metal oxide catalyst and steam;
   c. re-oxidizing the reduced metal oxide catalyst by introducing an oxygen containing gaseous oxidant to the reduced metal oxide catalyst; and
   d. re-using the re-oxidized metal oxide catalyst for a subsequent dehydrogenation and selective hydrogen combustion.

2. The process of claim 1, wherein the dehydrogenation reactants comprise an alkyl aromatic hydrocarbon or a substituted alkyl aromatic hydrocarbon and the dehydrogenated reaction product comprises an alkene aromatic hydrocarbon or substituted alkene aromatic hydrocarbon, respectively.

3. The process of claim 1, wherein the dehydrogenation reactants comprise an alkyl naphthalene and the dehydrogenated reaction product comprises an alkene naphthalene.

4. The process of claim 1, wherein the dehydrogenation reactants comprise an alkyl furan, alkyl pyrrole, alkyl thiophene, or alkyl pyridine, and the dehydrogenated product comprises alkene furan, alkene pyrrole, alkene thiophene, or alkene pyridine, respectively.

5. The process of claim 1, wherein the dehydrogenation reactants comprise a 1-butene or 2-butene, and the dehydrogenation product comprises 1,3-butadiene.

6. The process of claim 1 wherein the metal oxide catalyst is a redox catalyst comprising a catalytic dehydrogenation component and a hydrogen selective combustion component, wherein the catalytic dehydrogenation and hydrogen selective combustion components comprise a single metal oxide particle, two or more mixed metal oxides particles, or two or more independent metal oxides particles.

7. The process of claim 6, wherein the catalytic dehydrogenation component comprises one or more of:
i. potassium iron oxides selected from K—Fe—O, $K_2O/MeFe_2O_4$ (where Me=Mn, Cu, Co, Zn, or Ni), $K_2O/Ca_2Fe_2O_5$, and potassium-modified minerals;
ii. lithium iron oxides selected from Li—Fe—O, $Li_2O/MeFe_2O_4$ (where Me=Mn, Cu, Co, Zn, or Ni), $Li_2O/Ca_2Fe_2O_5$, and lithium-modified minerals;
iii. sodium iron oxides selected from Na—Fe—O, $Na_2O/MeFe_2O_4$ (where Me=Mn, Cu, Co, Zn, or Ni), $Na_2O/Ca_2Fe_2O_5$, and sodium-modified minerals;
iv. zinc iron oxides selected from Zn—Fe—O, $ZnO/MeFe_2O_4$ (where Me=Mn, Cu, Co, Zn, Ni), $ZnO/Ca_2Fe_2O_5$, and zinc-modified minerals; and
v. any combination or mixture thereof.

8. The process of claim 6, wherein the hydrogen selective combustion component comprises one or more of:
i. iron containing oxides selected from $MnFe_2O_4$ and $CuFe_2O_4$,
ii. vanadium oxides selected from $V_2O_5/MgOV_2O_5/TiO_2$—$ZrO_2$, and $V_2O_5/CeO_2$—$ZrO_2$;
iii. bismuth molybdate or molybdenum oxide;
iv. perovskite oxides or oxides selected from $ABO_3$, $A_2B_2O_5$, and $A_{n+1}B_nO_{3n+1}$ wherein A may be Ca, Sr, Ba, La, and/or other lanthanides, B may be a transition metal Mn or Fe and the A- or B-site may be partially substituted by rare metals, transition metal, alkali metals, and alkaline-earth metals;
v. mixed cerium oxides selected from $CeO_2$—$SmO_2$, and $CeO_2$—$ZrO_2$; and
vi. any combination or mixture thereof.

9. The process of claim 6, wherein the molar ratio of catalytic dehydrogenation component to hydrogen selective combustion component is from about 9:1 to about 1:9.

10. The process of claim 2, wherein the alkyl aromatic hydrocarbon is ethylbenzene or cumene, and the alkene aromatic hydrocarbon is styrene or α-methylstyrene, respectively.

11. The process of claim 1, wherein the metal oxide catalyst comprises one or more tailored metal oxide catalyst redox pair selected to enable near heat neutral or exothermic dehydrogenation, combustion, and re-oxidation.

12. The process of claim 1, wherein an inert heat transport carrier is provided during the dehydrogenation step, the selective hydrogen combustion step, or both, wherein the heat transport carrier maintains the thermal sufficiency of the environment during such step or steps.

13. The process of claim 12, wherein the inert heat transport agent exhibits one or more phase transitions during the dehydrogenation step, the selective hydrogen combustion step, or both, allowing for storage of heat beyond the heat capacity of the inert heat transport agent itself.

14. The process of claim 13, wherein the inert heat transport carrier is directly combined or mixed with the catalyst or coated on the surface of the catalyst to form combined particles.

15. A redox catalyst comprising a catalytic dehydrogenation component and a hydrogen selective combustion component,
wherein the catalytic dehydrogenation and hydrogen selective combustion components comprise a single metal oxide particle, two or more mixed metal oxides particles, or two or more independent metal oxides particles,
wherein the catalytic dehydrogenation component is capable of dehydrogenating a reactant to provide an olefinic compound and hydrogen,
wherein the hydrogen selective combustion component is capable of selectively combusting at least 50% of the hydrogen released during dehydrogenation to form a reduced metal oxide catalyst and steam.

16. The redox catalyst of claim 15, wherein the catalytic dehydrogenation component comprises one or more of:
i. potassium iron oxides selected from K—Fe—O, $K_2O/MeFe_2O_4$ (where Me=Mn, Cu, Co, Zn, or Ni), $K_2O/Ca_2Fe_2O_5$, and potassium-modified minerals;
ii. lithium iron oxides selected from Li—Fe—O, $Li_2O/MeFe_2O_4$ (where Me=Mn, Cu, Co, Zn, or Ni), $Li_2O/Ca_2Fe_2O_5$, and lithium-modified minerals;
iii. sodium iron oxides selected from Na—Fe—O, $Na_2O/MeFe_2O_4$ (where Me=Mn, Cu, Co, Zn, or Ni), $Na_2O/Ca_2Fe_2O_5$, and sodium-modified minerals;
iv. zinc iron oxides selected from Zn—Fe—O, $ZnO/MeFe_2O_4$ (where Me=Mn, Cu, Co, Zn, Ni), $ZnO/Ca_2Fe_2O_5$, and zinc-modified minerals; and
v. any combination or mixture thereof; and
wherein the hydrogen selective combustion component comprises one or more of:
i. iron containing oxides selected from $Fe_2O_3$, $Fe_3O_4$, $MnFe_2O_4$, $CuFe_2O_4$, and iron-rich minerals;
ii. vanadium oxides or vanadium-rich minerals;
iii. bismuth molybdate or molybdenum oxide;
iv. perovskite oxides or oxides selected from $ABO_3$, $A_2B_2O_5$, and $A_{n+1}B_nO_{3n+1}$ wherein A may be Ca, Sr, Ba, La, and/or other lanthanides, B may be a transition metal Mn or Fe, and the A- or B-site may be partially substituted by rare metals, transition metal, alkali metals, and alkaline-earth metals;
v. mixed cerium oxides selected from $CeO_2$—$SmO_2$, and $CeO_2$—$ZrO_2$; and
vi. any combination or mixture thereof.

17. The redox catalyst of claim 16, wherein the hydrogen selective combustion component is further modified by one or more modification agents comprising carbonate, alkali metal oxide/salts, sulfates, phosphates, molybdates, or tungstate to enhance the performance of selective hydrogen combustion.

18. The redox catalyst of claim 17, wherein the modification agent is a dispersion of two or more modification agents.

19. The redox catalyst of claim 18, wherein the dispersion further comprises a molten salt.

20. The process of claim 1, wherein an additional re-oxidation step is added between step b and step c to partially re-oxidize the metal oxide catalyst with steam or another soft oxidant.

* * * * *